US012678306B2

(12) United States Patent
Silverman et al.

(10) Patent No.: US 12,678,306 B2
(45) Date of Patent: Jul. 14, 2026

(54) ENDOPROSTHESES WITH INTERLOCKING STENTS HAVING VARYING STIFFNESS

(71) Applicant: W. L. Gore & Associates, Inc., Newark, DE (US)

(72) Inventors: James D. Silverman, Flagstaff, AZ (US); Tyson J. Skelton, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 920 days.

(21) Appl. No.: 17/793,885

(22) PCT Filed: Jan. 20, 2021

(86) PCT No.: PCT/US2021/014121
§ 371 (c)(1),
(2) Date: Jul. 19, 2022

(87) PCT Pub. No.: WO2021/150564
PCT Pub. Date: Jul. 29, 2021

(65) Prior Publication Data
US 2023/0050078 A1 Feb. 16, 2023

Related U.S. Application Data

(60) Provisional application No. 62/963,917, filed on Jan. 21, 2020.

(51) Int. Cl.
*A61F 2/915* (2013.01)
*A61F 2/89* (2013.01)

(52) U.S. Cl.
CPC ................ *A61F 2/915* (2013.01); *A61F 2/89* (2013.01); *A61F 2002/91575* (2013.01); *A61F 2210/0057* (2013.01)

(58) Field of Classification Search
CPC .... A61F 2/915; A61F 2/90; A61F 2/89; A61F 2/82; A61F 2/04; A61F 2210/0057; A61F 2002/828; A61F 2002/91583
See application file for complete search history.

(56) References Cited

U.S. PATENT DOCUMENTS

| | | |
|---|---|---|
| 4,776,337 A | 10/1988 | Palmaz |
| 5,383,892 A | 1/1995 | Cardon et al. |

(Continued)

FOREIGN PATENT DOCUMENTS

| | | |
|---|---|---|
| CN | 103561682 A | 2/2014 |
| JP | 2011-509151 A | 3/2011 |

(Continued)

OTHER PUBLICATIONS

US 6,413,270 B1, 07/2002, Thornton et al. (withdrawn)

(Continued)

*Primary Examiner* — Dinah Baria

(57) ABSTRACT

An endoprosthesis having a length, a first end, a second end, and a longitudinal axis is disclosed herein, where the endoprosthesis is expandable from a compact, delivery configuration to an enlarged, deployed configuration. The endoprosthesis includes a plurality of rows of stent elements along the length of the endoprosthesis, where the plurality of rows include a first row and a second row located adjacent to the first row. The first row of stent elements has a first plurality of alternating apices, and the second row of stent elements has a second plurality of alternating apices. The first and second pluralities of alternating apices define a spaced apart, interlocking arrangement. The endoprosthesis also includes a discontinuous web of material comprising a plurality of web elements spaced from one another and interconnecting the first and second pluralities of alternating apices. The plurality of web elements are arranged along a first, common circumference such that the plurality of web elements (Continued)

restrict torsion and axial compression of the endoprosthesis between the first and second rows of stent elements when the endoprosthesis is in the enlarged, deployed configuration.

13 Claims, 6 Drawing Sheets

(56)                    References Cited

U.S. PATENT DOCUMENTS

| | | | |
|---|---|---|---|
| 5,507,767 | A | 4/1996 | Maeda et al. |
| 5,735,892 | A | 4/1998 | Myers et al. |
| 7,258,697 | B1 | 8/2007 | Cox et al. |
| 7,306,729 | B2 | 12/2007 | Bacino et al. |
| 7,329,276 | B2 | 2/2008 | Smith et al. |
| 7,455,687 | B2 | 11/2008 | Saunders et al. |
| 7,691,461 | B1 | 4/2010 | Prabhu |
| 8,287,588 | B2 | 10/2012 | Leynov et al. |
| 8,500,794 | B2 | 8/2013 | Beach et al. |
| 8,926,688 | B2 | 1/2015 | Burkart et al. |
| 8,961,583 | B2 | 2/2015 | Hojeibane et al. |
| 9,089,446 | B2 | 7/2015 | Li et al. |
| 10,433,989 | B2 | 10/2019 | Garza et al. |
| 10,456,281 | B2 | 10/2019 | Armstrong et al. |

| | | | | |
|---|---|---|---|---|
| 2003/0083734 | A1 | | 5/2003 | Friedrich et al. |
| 2008/0281404 | A1* | | 11/2008 | Lee ........................... A61F 2/91 |
| | | | | 623/1.16 |
| 2009/0182413 | A1 | | 7/2009 | Burkart et al. |
| 2010/0010618 | A1 | | 1/2010 | Girton |
| 2010/0057187 | A1 | | 3/2010 | Caldarise et al. |
| 2014/0248418 | A1 | | 9/2014 | Eller et al. |
| 2016/0015538 | A1 | | 1/2016 | Kariniemi et al. |
| 2018/0125683 | A1 | | 5/2018 | Kariniemi et al. |

FOREIGN PATENT DOCUMENTS

| | | | |
|---|---|---|---|
| JP | 2017-521171 | A | 8/2017 |
| WO | 97/25937 | A1 | 7/1997 |
| WO | 2006/124824 | A1 | 11/2006 |

OTHER PUBLICATIONS

International Preliminary Report on Patentability received for PCT Patent Application No. PCT/US2021/014121, mailed on Aug. 4, 2022, 7 pages.

International Search Report and Written Opinion received for PCT Patent Application No. PCT/US2021/014121, mailed on May 11, 2021, 9 pages.

* cited by examiner

100

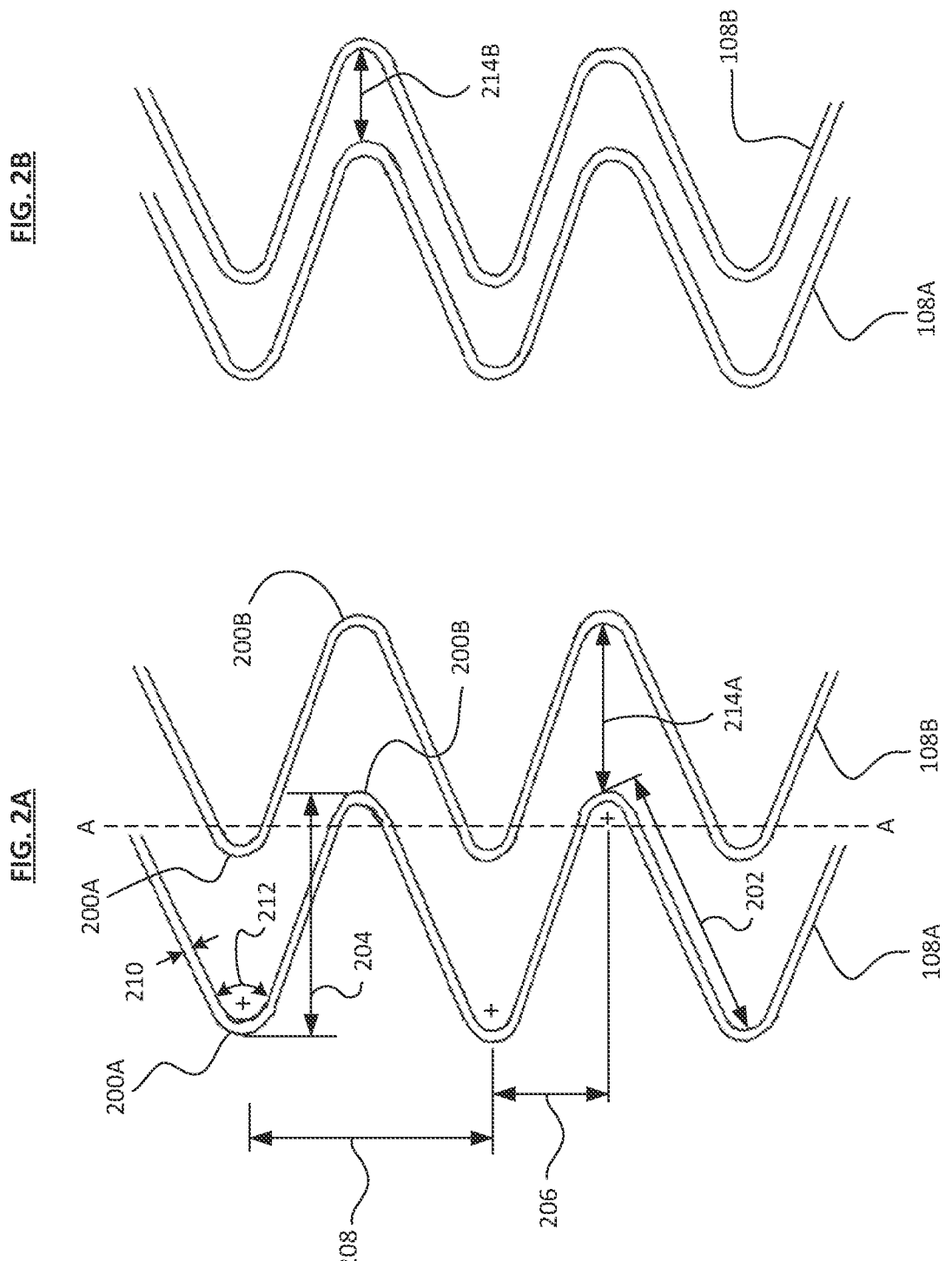

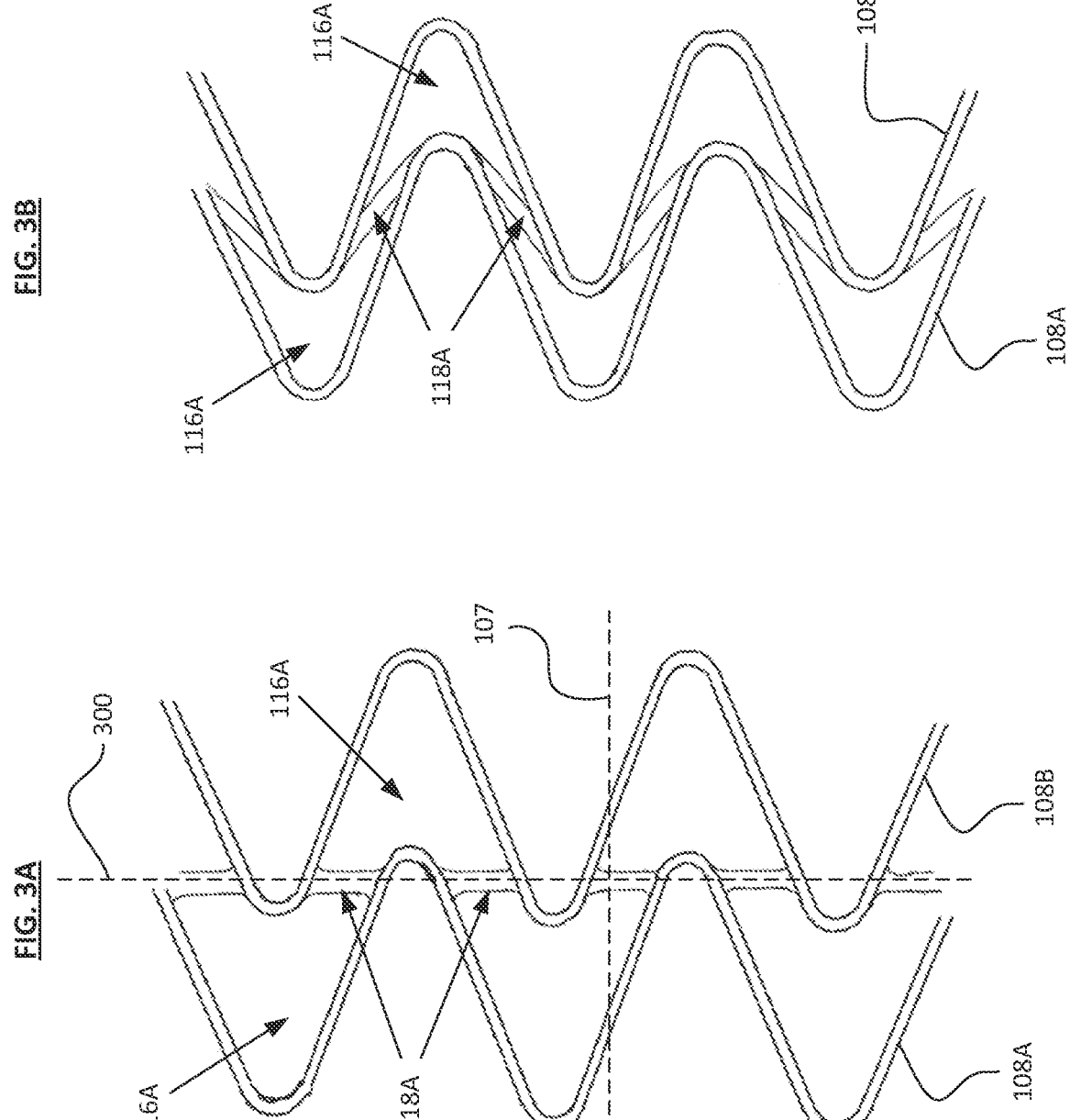

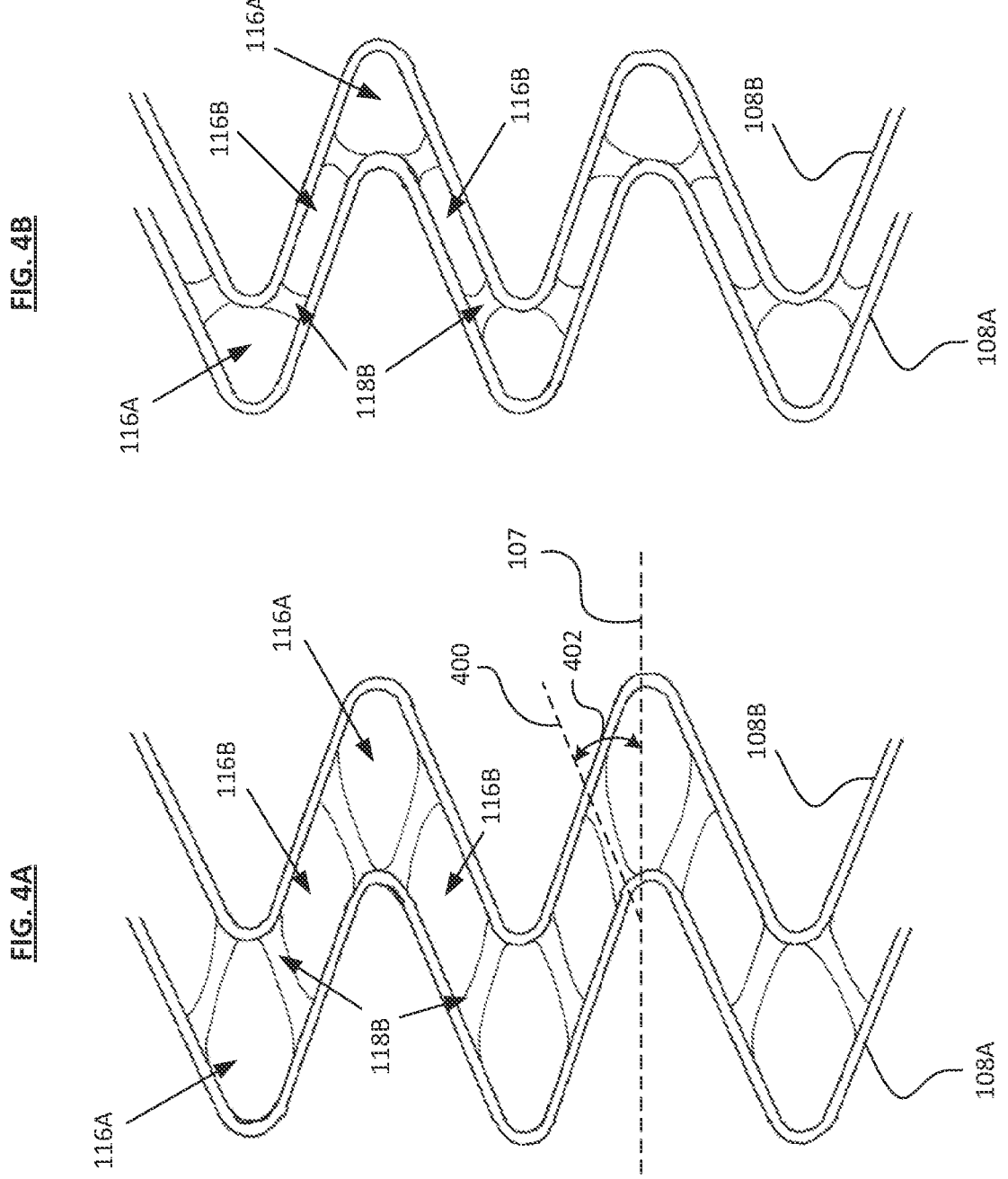

ENDOPROSTHESES WITH INTERLOCKING STENTS HAVING VARYING STIFFNESS

CROSS-REFERENCE TO RELATED APPLICATION

This application is a national phase application of PCT Application No. PCT/US2021/014121, internationally filed on Jan. 20, 2021, which claims the benefit of Provisional Application No. 62/963,917, filed Jan. 21, 2020, which are incorporated herein by reference in their entireties for all purposes.

FIELD

The present disclosure generally relates to implantable medical devices, and more particularly, to implantable stents having flexibly connected adjacent stent elements.

BACKGROUND

Implantable stents are typically required to have a small, compact diameter for insertion into an intended body conduit, typically via a catheter, to a desired site for deployment, at which site they are expanded to a larger diameter. Balloon expandable stents are expanded with an inflatable balloon. Self-expanding stents are restrained at a compact diameter by a constraining sleeve or other means and spring open upon release. Self-expanding stents are generally formed of shape memory, or super-elastic materials that are biocompatible. Nitinol stents are one common material employed for self-expanding stents.

The evolution of implantable stents has included the use of a tubular covering fitted to the stent. Covered stents have generally come to be referred to as stent-grafts. As an alternative to a continuous, or substantially continuous covering (e.g., substantially fluid impermeable covering), flexible elements (e.g., film or membrane material) may be employed to interconnect stent elements while leaving openings between the flexible elements. U.S. Pat. No. 8,926,688 to Burkart et al., entitled "Stent Having Adjacent Elements Connected by Flexible Webs," describes such alternatives to covered stents. Burkart et al. describes stents incorporating flexible, preferably polymeric, connecting elements wherein these elements connect adjacent, spaced-apart stent elements.

Generally, a fully covered stent-graft can be considered to have a surface area (hereinafter $A_{max}$) equal to the outer circumference of the expanded stent multiplied by the length of the stent. For a conventional, open frame stent (as opposed to a stent-graft), the surface area represented by all of the stent elements is only a small portion of the maximum surface area $A_{max}$. The actual surface area covered by the stent, meaning the area covered by all components of the stent (including connecting elements) in their deployed state, is $A_{stent}$. The porosity index, or P.I., describes the open area (the portion of the maximum surface area not covered by all components of the stent assembly) as a percentage of maximum surface area, wherein: $P.I.=(1-(A_{stent}/A_{max}))\times 100\%$.

Some methods of measuring the actual surface area covered by the stent ($A_{stent}$), involves the use of a machine provided Visicon Inspection Technologies, LLC (Napa, Calif.). The Visicon Finescan™ Stent Inspection System (Visicon Finescan machine model 85) uses a 6000 pixel line scan camera to generate a flat, unrolled view of a stent. In operation, the stent is mounted on a sapphire mandrel with a fine diffuse surface. This mandrel is held under the linear array camera and rotated by the system electronics and is used to trigger the linear array camera to collect a line of image data in a precise line-by-line manner. After a complete revolution an entire image of the stent is acquired. When the entire stent has been imaged, the software differentiates between the stent with cover and the background. The total number of picture elements (pixels) is compared to the total number of pixels associated with the stent and cover to determine $A_{stent}$. Basic settings on the machine used for this type of determination are (for example): light, 100%; exposure, 0.3 ms/line; gain, 5; threshold, 50; noise filter, 20; smoothing, 4.

The open area may be a continuous single space, such as the space between windings of a single helically wound stent element. Likewise the open area may be represented by the space between multiple individual annular or ring-shaped stent elements. The open area may also be represented by the total area of multiple apertures provided by either a single stent element (e.g., as shown by FIGS. 1B and 2B of U.S. Pat. No. 4,776,337 to Palmaz) or by multiple stent elements providing multiple apertures. If multiple apertures are provided, they may be of equal or unequal sizes. The use of a perforated graft covering or of polymeric elements in addition to metallic stent elements may also reduce the open area.

Stents having a porosity index of greater than 50% are considered to be substantially open stents.

In addition to the porosity index, the size of any aperture providing the open area must be considered if it is intended to cover only a portion of a stent area for a specific stent application. For multiple apertures, often the consideration must be for the largest size of any individual aperture, particularly if the apertures are to provide for a "filtering" effect whereby they control or limit the passage of biologic materials from the luminal wall into the flow space of the body conduit.

Various stent devices combining metallic stent elements with polymeric connecting elements are known; see, for example U.S. Pat. No. 5,507,767 to Maeda et al. Another is a stent provided with a flexible knitted sleeve having small open apertures in the fashion of chain link fencing, from InspireMD Ltd. (4 Derech Hashalom St., Tel Aviv 67892 Israel).

SUMMARY

According to one example ("Example 1"), an endoprosthesis has a length, a first end, a second end, and a longitudinal axis, where the endoprosthesis is expandable from a compact, delivery configuration to an enlarged, deployed configuration. The endoprosthesis includes a plurality of rows of stent elements along the length of the endoprosthesis, where the plurality of rows include a first row and a second row located adjacent to the first row. The first row of stent elements has a first plurality of alternating apices, and the second row of stent elements has a second plurality of alternating apices. The first and second pluralities of alternating apices define a spaced apart, interlocking arrangement. The endoprosthesis also includes a discontinuous web of material comprising a plurality of web elements spaced from one another and interconnecting the first and second pluralities of alternating apices. The plurality of web elements are arranged along a first, common circumference such that the plurality of web elements restrict torsion and axial compression of the endoprosthesis between the first and second rows of stent elements when the endoprosthesis is in the enlarged, deployed configuration.

According to another example ("Example 2") further to Example 1, the discontinuous web of material further includes a second plurality of web elements spaced from one another and interconnecting the first and second pluralities of alternating apices. The second plurality of web elements are arranged along a second, common circumference longitudinally spaced from the first, common circumference such that the second plurality of web elements restrict torsion and elongation of the endoprosthesis between the first and second rows of stent elements when the endoprosthesis is in the enlarged, deployed configuration.

According to another example ("Example 3"), further to Example 1 or 2, the discontinuous web of material is a polymeric film defining a plurality of apertures between the first and second rows of stent elements.

According to another example ("Example 4"), further to any one of Examples 1 to 3, the plurality of web elements and, optionally, the second plurality of web elements, each extend at an angular offset relative to the circumference of the endoprosthesis.

According to another example ("Example 5"), further to any one of Examples 1 to 4, circumferentially-adjacent ones of the plurality of web elements extend at alternating, opposite angles relative to one another.

According to another example ("Example 6"), further to any one of Examples 1 to 5, the plurality of web elements, and, optionally, the second plurality of web elements, each extend at an acute angular offset relative to the circumference of the endoprosthesis when the endoprosthesis is in the enlarged, deployed configuration.

According to another example ("Example 7"), further to any one of Examples 1 to 6, the plurality of web elements each extend at an obtuse angle relative to the longitudinal axis of the endoprosthesis when the endoprosthesis is in the enlarged, deployed configuration.

According to another example ("Example 8"), further to any one of Examples 1 to 3, the plurality of web elements, and, optionally, the second plurality of web elements, each extend along a circumference of the endoprosthesis.

According to another example ("Example 9"), further to any one of Examples 1 to 7, the first and second rows of stent elements and the plurality of web elements interconnecting the first and second pluralities of alternating apices of the first and second rows of stent elements are located within a first section along the length of the endoprosthesis. Furthermore, a second section of the endoprosthesis along the length of the endoprosthesis includes a third row of stent elements having alternating apices and a fourth row of stent elements having alternating apices. The third and fourth rows define a spaced apart arrangement when the endoprosthesis is in the enlarged, deployed configuration. The endoprosthesis includes a second discontinuous web of material interconnecting the third and fourth row of stent elements such that the endoprosthesis is axially compressible between the third and fourth rows of stent elements when the endoprosthesis is in the enlarged, deployed configuration.

According to another example ("Example 10"), further to Example 9, the second discontinuous web of material includes a plurality of web elements each extending at an acute angle with respect to the longitudinal axis of the endoprosthesis.

According to another example ("Example 11"), further to Example 9 or 10, the first section is adjacent the first end of the endoprosthesis and the second section is located closer to a mid-point between the first and second ends of the endoprosthesis than the first section.

According to another example ("Example 12"), further to any one of Examples 9 to 11, the endoprosthesis is more axially rigid at the first section than at the second section when the endoprosthesis is in the enlarged, deployed configuration.

According to another example ("Example 13"), further to any one of Examples 9 to 12, the endoprosthesis also includes a third section toward the second end of the endoprosthesis that is as axially rigid as the first section.

According to another example ("Example 14"), further to any one of Examples 9 to 13, the third and fourth rows define a spaced apart, interlocking arrangement when the endoprosthesis is in the enlarged, deployed configuration.

According to another example ("Example 15"), further to any one of Examples 9 to 13, the third and fourth rows define a spaced apart, non-interlocking arrangement when the endoprosthesis is in the enlarged, deployed configuration.

According to another example ("Example 16"), further to any one of Examples 1 to 15, the plurality of rows of stent elements are formed of an elastically deformable material, optionally, a nickel-titanium alloy.

According to another example ("Example 17"), further to any one of Examples 1 to 16, the plurality of rows of stent elements are formed of a plastically deformable material, optionally, a stainless steel alloy.

According to another example ("Example 18"), further to any one of Examples 1 to 17, the discontinuous web of material comprises a thin film.

According to another example ("Example 19"), further to any one of Examples 1 to 18, the discontinuous web of material comprises an ePTFE membrane.

According to another example ("Example 20"), further to any one of Examples 1 to 19, the first plurality of alternating apices are axially aligned with the second plurality of alternating apices to define a plurality of interlocked peaks and a plurality of interlocked valleys.

The foregoing Examples are just that, and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIG. 2A illustrates two adjacent stent elements of an endoprosthesis in an enlarged, deployed configuration without flexible bridges shown, according to some embodiments.

FIG. 2B illustrates two adjacent stent elements of an endoprosthesis in a compact, delivery configuration without flexible bridges shown, according to some embodiments.

FIG. 3A illustrates two adjacent stent elements of an endoprosthesis in an enlarged, deployed configuration, with flexible bridges connecting the adjacent stent elements along a common circumference, according to some embodiments.

FIG. 3B illustrates the two adjacent stent elements of the endoprosthesis of FIG. 3A in a compact, delivery configuration, according to some embodiments.

FIG. 4A illustrates two adjacent stent elements of an endoprosthesis in an enlarged, deployed configuration with bridges extending at an acute angle with respect to a longitudinal axis of the endoprosthesis, according to some embodiments.

FIG. 4B illustrates the adjacent stent elements of FIG. 4A with the endoprosthesis in a compact, delivery profile, according to some embodiments.

Figure 1A:
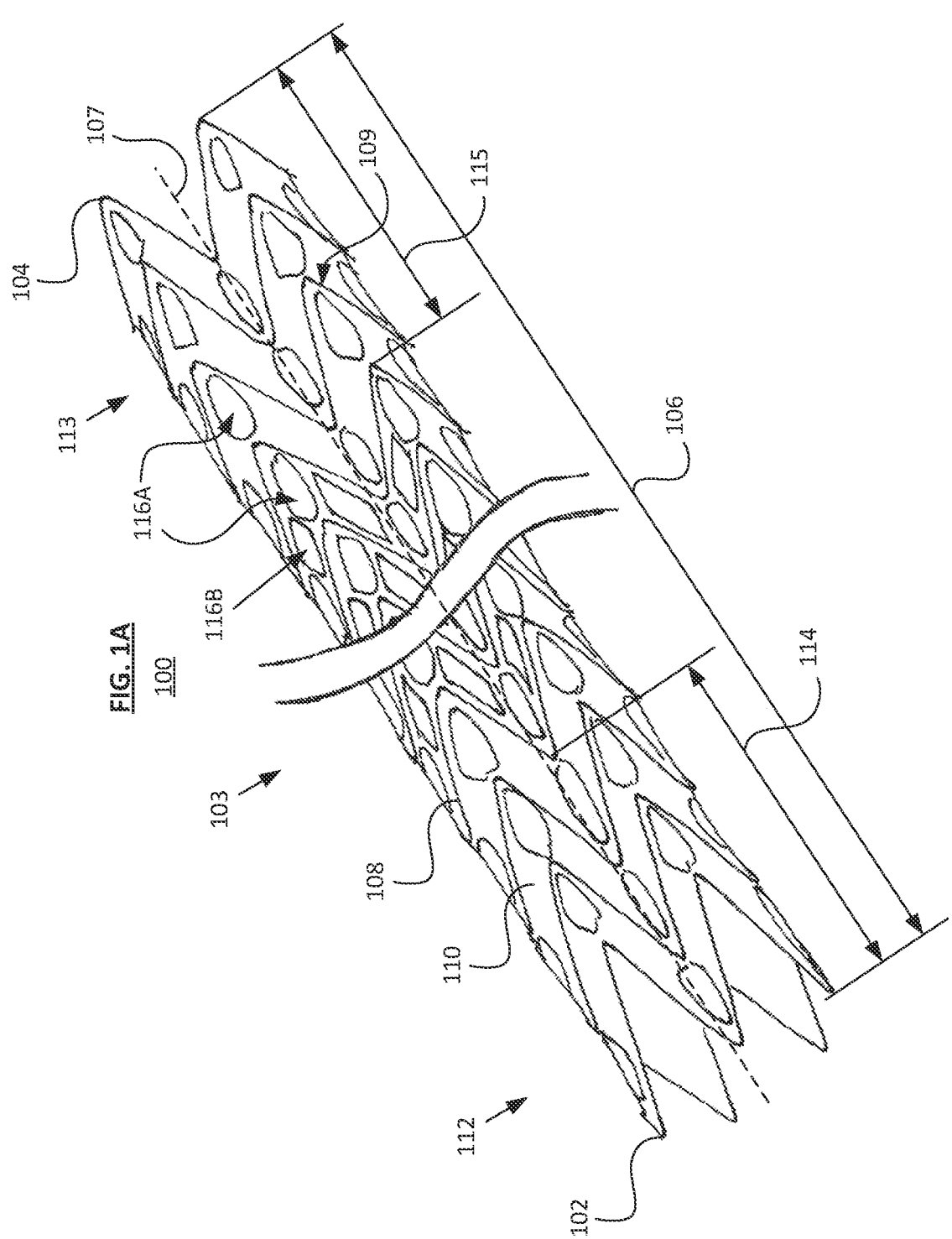
FIG. 1A is a perspective view of an endoprosthesis, according to some embodiments.

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

DETAILED DESCRIPTION

Figure 1B:
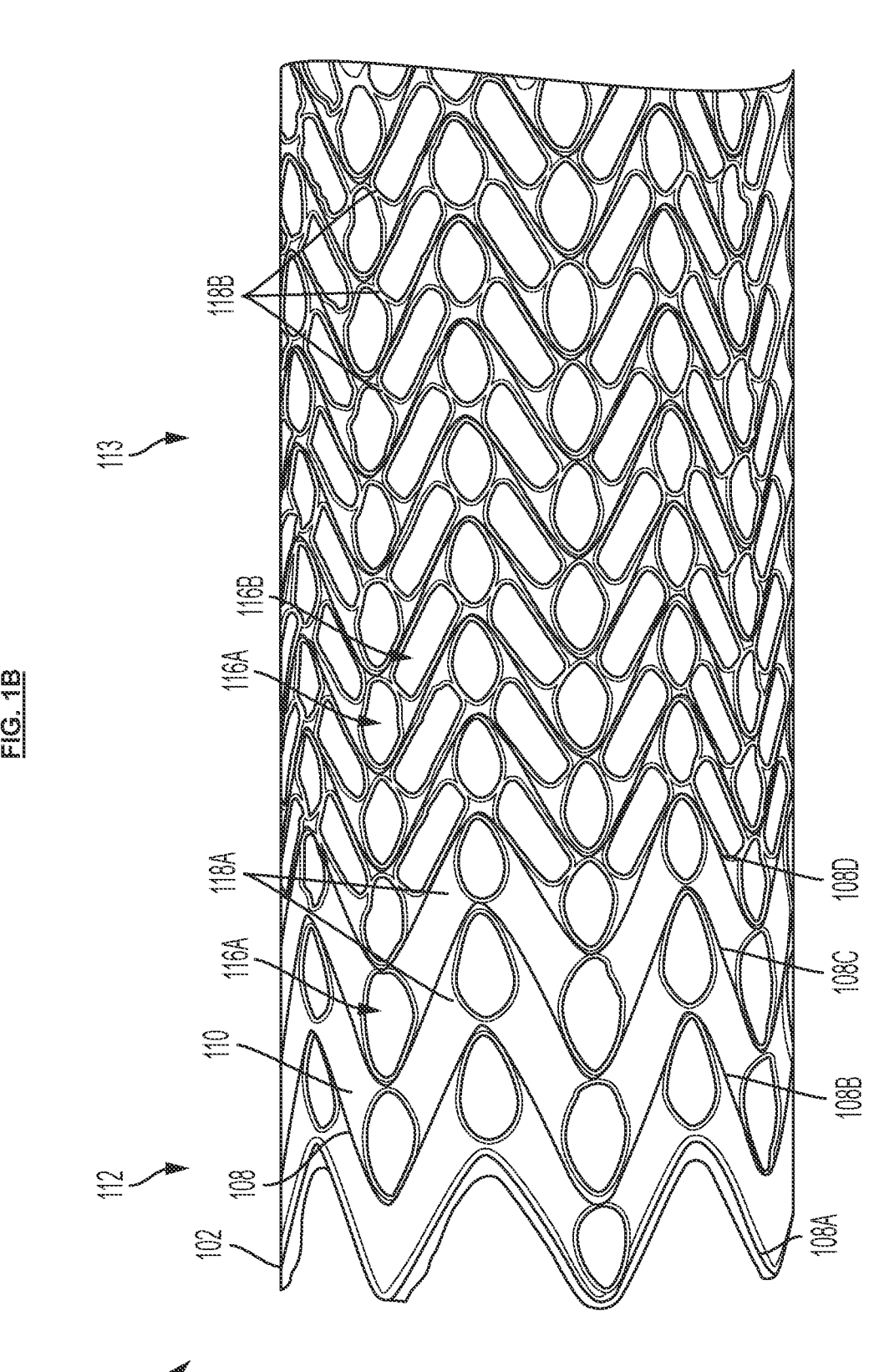
FIG. 1B is another view of an endoprosthesis, according to some embodiments.

FIGS. 1A and 1B show an implantable medical device or, more specifically, an endoprosthesis 100 that has a first end 102, a second end 104, and an intermediate portion 103, which may include a midpoint located between the first and second ends 102 and 104, extending therebetween. The endoprosthesis 100 has a longitudinal length 106 measured from the first end 102 to the second end 104. The endoprosthesis 100 has a plurality of rows of stent elements 108 along the length 106 thereof and a web of material, or web 110 (for example, a flexible polymeric material) connecting between neighboring rows of the stent elements 108. The stent elements 108 are interlocked with one another, as further explained below. The endoprosthesis 100 also defines a longitudinal axis 107 extending along the length of the endoprosthesis 100.

In some examples, the rows of stent elements 108 are formed by a serpentine, or undulating length of an elongate element (e.g., a filament or wire material) extending in a helical path about the circumference of the endoprosthesis 100 along the length of the endoprosthesis 100. Each sequential turn, pass, or winding of the elongate element 109 results in the spaced-apart, adjacent rows of stent elements 108 as shown. In some examples, the elongate element 109 extends continuously between opposing ends (the first end 102 and the second end 104) of the endoprosthesis 100. Although a continuous, helical winding is contemplated, other configurations are also contemplated. For example, discrete (e.g., circumferential) rings may also be employed to define adjacent rows of stent elements 108. In some examples, the stent elements 108 may be formed of an elastically deformable material, such as a nickel-titanium alloy. In some examples, the stent elements 108 may be formed of a plastically deformable material, such as a stainless steel alloy and/or otherwise be configured to be plastically deformed during deployment.

The web 110 is discontinuous over its length due to a plurality of apertures or openings 116 formed therein. The discontinuity in the web 110 allows for the web 110 to provide sufficient flexibility that allows the stent elements 108 to move relative to each other. The movement of the stent elements 108 relative to each other causes the overall length 106 of the endoprosthesis 100 to increase or decrease, allow for the endoprosthesis 100 to assume a compact delivery profile with a smaller length 106 or an enlarged deployed profile with a larger length 106.

The stent elements 108 also include a first section 112 adjacent to the first end 102 and/or the second end 104. In the first section 112, the web 110 is configured to restrict movement of the stent elements 108 relative to one another. That is, the first section 112 is configured to be relatively stiffer than some of the other sections of the endoprosthesis 100, such as an intermediate portion of the endoprosthesis 100.

FIG. 1A shows the first section 112 adjacent to the first end 102, a second section 113, and a third section 115 adjacent to the second end 104, where the second section 113 is located between the first section 112 and the third section 115 such that the web 110 at the first section 112 and the third section 115 is configured such that relative movement of the stent elements 108 in the third section are restricted relative to one another.

The first section 112 and/or the third section 115 may be stiffer or more axially rigid than the second section 113 that is located closer to the midpoint of the endoprosthesis 100 than the other sections. The first section 112 and the third section 115 may be similar to one another in terms of stiffness and axial rigidity, or may differ as desired.

The web 110 has a plurality of apertures or openings 116A and 116B along the length 106 of the endoprosthesis 100. As shown, the web 110 in the first section 112 and/or the third section 115 has a larger surface area coverage or contains less open area than in other portions (e.g., the second section 113) of the endoprosthesis 100. In some examples, the set of openings 116A are located evenly throughout the length 106 of the endoprosthesis 100, but the first section 112 and/or the third section 115 may include fewer or smaller openings (e.g., being without the additional openings 116B) in the second section 113 of the endoprosthesis 100.

As shown in FIG. 1B, having less open area in the web 110 allows for a broader interconnecting member or web element, also referred to as a bridge 118A. As shown, the first section 112 has a first set of web elements or bridges 118A that differs from a second set of web elements or bridges 118B found in the second section 113. The web elements or bridges 118A and 118B may be a polymeric film that define the sets of openings 116A and/or 116B. In some examples, the web elements or bridges 118A and 118B may be made of a thin film ranging between approximately 0.001 mm to 0.1 mm, 0.1 mm to 0.2 mm, 0.2 mm to 0.5 mm, or any other suitable thickness thereof. In FIG. 1B, the first set of bridges 118A is broader in width than the second set of bridges 118B because the first section 112 does not have the second set of openings 116B between the first set of openings 116A. The first section 112 in this case is defined by a set of four stent elements 108A, 108B, 108C, and 108D, although there may be fewer or more stent elements in the first section 112 in other examples. The second stent element 108B may be adjacent to the first stent element 108A, the third stent element 108C may be adjacent to the second stent element 108B, and so on.

Each of the stent elements 108 (e.g., stent elements 108A, 108B, 108C, 108D, for example), may extend at an angular offset relative to the circumference (for example, center line A-A) of the endoprosthesis 100. In some examples, the third stent element 108C and the fourth stent element 108D may define a spaced apart arrangement when the endoprosthesis 100 is in the enlarged, deployed configuration. There may also be a second discontinuous web of material interconnecting the third and fourth stent elements 108C and 108D such that the endoprosthesis 100 is axially compressible between the third and fourth stent elements 108C and 108D when the endoprosthesis 100 is in the enlarged, deployed configuration. Also, in some examples, when the endoprosthesis 100 is in the enlarged, deployed configuration, the rows of stent elements 108A and 108B may be in a spaced-apart, interlocking arrangement with one another and the rows of stent elements 108C and 108D may be in a spaced-apart, non-interlocking arrangement with one another.

FIGS. 2A and 2B show details of the elongate element 109 shown in FIGS. 1A and 1B when the endoprosthesis 100 is in either the enlarged deployed profile, or configuration or the compact delivery profile, or configuration. Opposing apices 200A and 200B are interconnected by straight or relatively straight elongate element segments 202. The apices typically "point" in directions that are substantially parallel to a longitudinal axis 107 of the endoprosthesis 100 (e.g., within 10 degrees of parallel), with alternating apices 200A and 200B pointing in opposite directions. That is, the alternating apices 200A and 200B point to opposite ends of the endoprosthesis 100. In some examples, apices pointing in one direction (e.g., apices 200A) are aligned along a first common line while the apices pointing in the opposite direction (e.g., apices 200B) are aligned along a second common line that is parallel to the first common line. For example, the alternating apices 200A may be axially aligned with one another to define a plurality of interlocked valleys, and the alternating apices 200B may also be axially aligned with one another to define a plurality of interlocked peaks, or vice versa.

As previously mentioned, some or all of the rows of the stent elements 108 along at least a portion of the length 106 of the endoprosthesis 100 are interlocked with one another. In the context of this disclosure, the term "interlocked" or "interlocking" is defined as when portions of two adjacent or neighboring stent elements (for example, 108A and 108B as shown) cross over across a center line or circumference (A-A) located midway between the two stent elements and extending or directing perpendicularly to the longitudinal axis 107, when the endoprosthesis 100 is in the enlarged deployed profile. That is, as shown in FIG. 2A, the center line A-A passes through the stent elements 108A and 108B such that the left-pointing apex 200A (which may be referred to as a valley) from the stent element 108B and the right-pointing apex 200B (which may be referred to as a peak) from the stent element 108A cross over across the center line A-A. Furthermore, in some examples, the adjacent rows of stent elements 108 may be in interlock with one another along the entire length 106 of the endoprosthesis 100. Alternatively, there may be one or more rows of stent elements 108 that are not in interlock with the other adjacent row(s) thereof along one or more portions along the length 106 of the endoprosthesis 100.

FIG. 2A shows two adjacent stent elements (108A and 108B) when the endoprosthesis 100 is in an enlarged deployed profile, e.g. when the rows of stent elements 108 are spaced farther apart than in the compact delivery profile. Dimension 204 is considered as the height (amplitude) of adjacent opposing apices while dimension 206 is the width of adjacent opposing apices. Dimension 208 describes one full period of the serpentine form. Elongate element diameter 210 and bend angle 212 of the apices 200A, 200B may be chosen as appropriate. Furthermore, the apices 200A, 200B may have any suitable radius of curvature. Dimension 214A describes the distance between neighboring rows of stent elements 108 when the endoprosthesis 100 is in the enlarged deployed profile, which may be measured from the apex 200A of the first stent element 108A to the nearest apex 200A (not apex 200B which points in the opposite direction from apex 200A) of the second stent element 108B, for example. FIG. 2B shows when the endoprosthesis 100 is in the compact delivery profile in which dimension 214B which is the distance between neighboring rows of stent elements 108A and 108B when the endoprosthesis 100 is in the compact deployment profile.

FIGS. 3A and 3B show an example of how the openings 116A and bridges 118A may be configured in the first section 112 and/or the third section 115, according to some embodiments. FIG. 3A shows the openings 116A and bridges 118A when the endoprosthesis 100 is in the enlarged deployed profile where the stent elements 108A and 108B are farther apart from one another than in the compact delivery profile shown in FIG. 3B. The bridges 118A are formed such that each of the bridges 118A formed between the stent elements 108A and 108B encompasses a circumferential reference line or circumference 300 that is directed substantially perpendicular to the longitudinal axis 107 of the endoprosthesis 100. In some examples, the circumferential reference line that defines the circumference of the endoprosthesis 100 extends circumferentially around the longitudinal axis 107. As such, in some examples, the circumference 300 crosses all the bridges 118A, thereby making it a common circumference 300 among the bridges 118A such that the bridges 118A restrict torsion and axial compression of the endoprosthesis 100 between the first and second rows (e.g., 108A and 108B) of stent elements when the endoprosthesis 100 is in the enlarged, deployed configuration. In some examples, the angle formed between the circumference 300 and the longitudinal axis 107 may range between about 75° and 90°, about 80° and 90°, about 85° and 90°, or any other suitable range of obtuse angles therebetween. Furthermore, in some examples, the circumference 300 may overlap with the center line A-A previously shown in FIG. 2A.

In FIG. 3B, the two adjacent stent elements 108A and 108B are brought closer together, causing the bridges 118A to be stretched or tensioned. When the web 110 is made of a flexible, relatively inextensible polymeric material, the bridges 118A resist such axial compression. But, in examples where the web 110 is made of an elastically extensible material, the bridges 118A store potential energy upon such axial compression, resist such compression, and bias the rows of stent elements 108A and 108B back to their original position shown in FIG. 3A. Therefore, in some examples, the bridges 118A may restrict the movement of the stent elements 108A and 108B relative to one another. Notably, when the rows of stent elements 108A and 108B are radially collapsed (e.g., when the endoprosthesis is in the compact, delivery profile) the bridges 118A are free to flex or angulate and do not prevent or resist axial compression between the rows of the stent elements 108A and 108B.

Figure 3C:
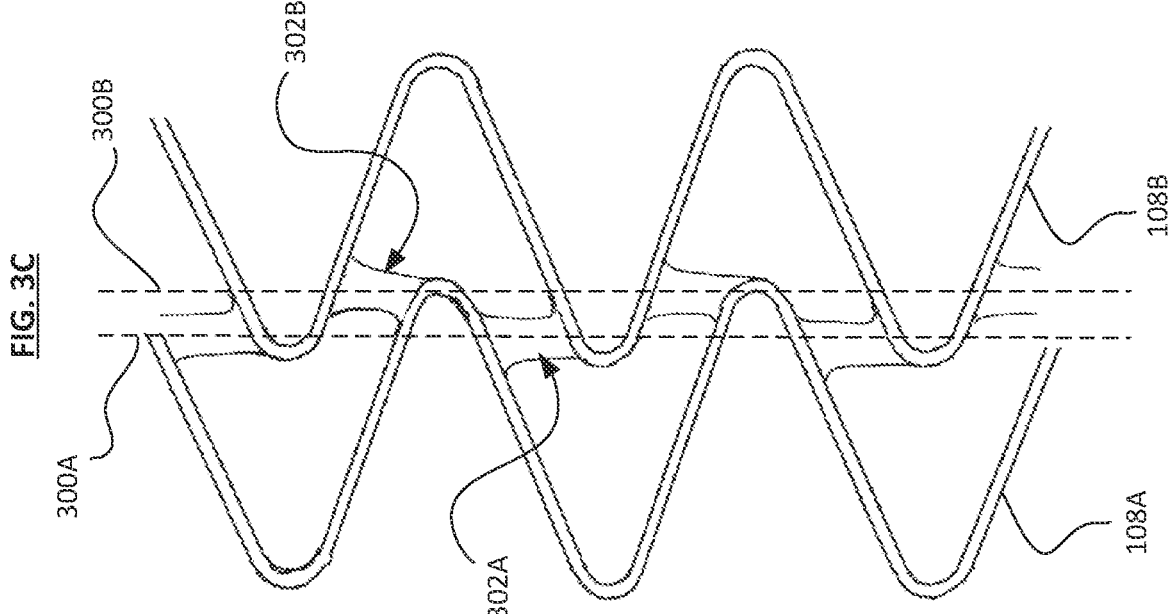
FIG. 3C illustrates two adjacent stent elements of another endoprosthesis in an enlarged, deployed configuration, with flexible bridges connecting the adjacent stent elements along two common circumferences, according to some embodiments.

FIG. 3C shows an example of how bridges 302A and 302B may be configured in the first section 112 and/or the third section 115, according to some embodiments. Unlike the bridges 118A in FIGS. 3A and 3B, the bridges 302A and 302B encompass a plurality of circumferences that are substantially parallel to one another. Specifically, the bridges 302A share a first circumference 300A that is common amongst the bridges 302A, and the bridges 302B include a second circumference 300B that is common amongst the bridges 302B, in which the first circumference 300A and the second circumference 300B are parallel to one another. As such, the first plurality of bridges 302A and the second plurality of bridges 302B restrict torsion and elongation of the endoprosthesis 100 between the first and second rows of stent elements 108 when the endoprosthesis 100 is in the enlarged, deployed configuration. The positions of the bridges 302A and 302B may be described as being in a "staggered" configuration with respect to one another in that there is not a single straight line that passes through all the bridges 302A and 302B. In some examples, each of the bridges 118A (or 302A and 302B) may extend at an acute angular offset relative to the circumference 300 of the endoprosthesis 100 when the endoprosthesis 100 is in the enlarged, deployed configuration. In some examples, each of the bridges 118A (or 302A and 302B) may extend at an obtuse angle relative to the longitudinal axis 107 of the endoprosthesis 100 when the endoprosthesis 100 is in the enlarged, deployed configuration.

FIGS. 4A and 4B show an example of how the openings 116B and bridges 118B may be configured in the second section 113, according to some embodiments. In some examples, circumferentially-adjacent bridges 118B extend at alternating, opposite angles relative to one another. FIG. 4A shows the openings 116A and 116B as well as the bridges 118B when the endoprosthesis 100 is in the enlarged deployed profile. Each of the bridges 118B is formed to encompass a line 400 positioned at an angle different from the bridges 118A. For example, each of the bridges 118B is positioned at an acute angle 402 with respect to the longitudinal axis 107 of the endoprosthesis 100. In some examples, the acute angle 402 may range between about 5° and 10°, about 5° and 20°, about 5° and 30°, about 5° and 45° or any other suitable range of angles therebetween.

When the stent elements 108A and 108B are brought closer together relative to each other as shown in FIG. 4B, the length of each of the bridges 118B decreases. As such, there is no tension force applied to the bridges 118B in this state, so there is no stretching, tensioning, or other substantial storage of potential energy in the bridges 118B to restrict the movement of the stent elements 108A and 108B relative to one another.

While various polymeric films may be suitable for use as the stent covering (or coating) material for this device, as well as for the web of material used to define the bridges in the endoprosthesis, combinations of FEP (fluorinated ethylene propylene) films used in combination with ePTFE films or membranes may be contemplated. The ePTFE films for use with the stent elements are films having multiaxial fibrillar orientations as shown by the scanning electron photomicrograph of FIG. 3. It is seen how the fibrils are oriented in all directions within the plane of the ePTFE film. ePTFE films of this type may be made as taught by U.S. Pat. No. 7,306,729 and US Published Patent Application 2007/0012624 to Bacino et al. Films of this same type may optionally be provided with a partial covering of a thin layer of FEP (having openings through the FEP film covering; i.e., a discontinuous covering). FEP coated ePTFE films, with either a discontinuous (porous) FEP covering (coating) or a continuous (non-porous) FEP covering (coating) may be made generally as taught by U.S. Pat. No. 5,735,892 to Myers et al.

In some examples, the stiffness of the bridges 118A in the first section 112 and/or the third section 115 may be increased by applying one or more additional material to the bridges 118A. For example, in addition to the web 110, a secondary material such as another layer of polymer as explained above or a fibrous material, as well as any other suitable material, may be attached to the bridges 118A to restrict movement of the rows of stent elements 108 relative to one another in the first section 112 and/or the third section 115. In some examples, the additional material applied to the bridges 118A may be the same material from which the web 110 is made.

Advantages in increasing the stiffness to restrict movement of the stent elements relative to one another at or near the end sections include preventing foreshortening of the stent elements during expansion as the stent elements are deformed. In some examples, the endoprosthesis is mounted on a balloon for subsequent deployment and expansion, but if the balloon expands unevenly, the stent elements of the endoprosthesis may experience foreshortening or accordioning at regions proximal to the ends of the endoprosthesis. Having the regions proximal to the ends of the endoprosthesis be stiffer, or more rigid, during expansion reduces the likelihood of such undesired changes in the shape of the endoprosthesis.

The embodiments have been described above both generically and with regard to specific embodiments. It will be apparent to those skilled in the art that various modifications and variations can be made in the embodiments without departing from the scope of the disclosure. Thus, it is intended that the embodiments cover the modifications and variations of the embodiments provided they come within the scope of the appended claims and their equivalents.

What is claimed is:

1. An endoprosthesis having a length, a first end, a second end, and a longitudinal axis, the endoprosthesis being expandable from a compact, delivery configuration to an enlarged, deployed configuration, the endoprosthesis comprising:

a plurality of rows of stent elements along the length of the endoprosthesis, the plurality of rows including a first row and a second row located adjacent to the first row, the first row of stent elements having a first plurality of alternating apices and the second row of stent elements having a second plurality of alternating apices, the first and second pluralities of alternating apices defining a spaced apart, interlocking arrangement in the compact, delivery configuration and in the enlarged, deployed configuration; and a discontinuous web of material comprising a thin film, the discontinuous web of material defining a plurality of web elements spaced from one another and interconnecting the first and second pluralities of alternating apices, the plurality of web elements being arranged along a circumference such that an angle formed between the circumference and the longitudinal axis is from 75 degrees to 90 degrees;

wherein, when the endoprosthesis is in the enlarged, deployed configuration, the plurality of web elements restrict torsion and axial compression of the endoprosthesis between the first and second rows of stent elements.

2. The endoprosthesis of claim 1, wherein the plurality of web elements and the first and second rows of stent elements define a plurality of apertures.

3. The endoprosthesis of claim 1, wherein the plurality of rows of stent elements are formed of an elastically deformable material.

4. The endoprosthesis of claim 3, wherein the elastically deformable material includes a nickel-titanium alloy.

5. The endoprosthesis of claim 1, wherein the thin film comprises an ePTFE membrane.

6. The endoprosthesis of claim 1, wherein the first plurality of alternating apices are axially aligned with the second plurality of alternating apices to define a plurality of interlocked peaks and a plurality of interlocked valleys.

7. The endoprosthesis of claim 1, wherein the plurality of rows of stent elements are formed of a plastically deformable material.

8. The endoprosthesis of claim 7, wherein the plastically deformable material includes a stainless steel alloy.

9. An endoprosthesis having a length, a first end, a second end, and a longitudinal axis, the endoprosthesis being expandable from a compact, delivery configuration to an enlarged, deployed configuration, the endoprosthesis comprising:

a plurality of rows of stent elements along the length of the endoprosthesis, the plurality of rows including a first row and a second row located adjacent to the first row, the first row of stent elements having a first plurality of alternating apices and the second row of stent elements having a second plurality of alternating apices, the first and second pluralities of alternating apices defining a spaced apart, interlocking arrangement; and a discontinuous web of material comprising:

a first plurality of web elements spaced from one another and interconnecting the first and second pluralities of alternating apices, the first plurality of web elements being arranged along a first, common circumference, and a second plurality of web elements spaced from one another and interconnecting the first and second pluralities of alternating apices, the second plurality of web elements being arranged along a second, common circumference longitudinally spaced from the first, common circumference;

wherein, when the endoprosthesis is in the enlarged, deployed configuration, the first plurality of web elements and the second plurality of web elements restrict torsion and elongation of the endoprosthesis between the first and second rows of stent elements.

10. The endoprosthesis of claim 9, wherein one or more of the first plurality of web elements and the second plurality of web elements each extend at an angular offset relative to the circumference of the endoprosthesis.

11. The endoprosthesis of claim 9, wherein one or more of the first plurality of web elements and the second plurality of web elements each extend at an acute angular offset relative to the circumference of the endoprosthesis when the endoprosthesis is in the enlarged, deployed configuration.

12. The endoprosthesis of claim 9, wherein one or more of the first plurality of web elements and the second plurality of web elements each extend along a circumference of the endoprosthesis.

13. The endoprosthesis of claim 9, wherein the first plurality of web elements are arranged at a first angle from 75 degrees to 90 degrees with respect to the longitudinal axis along the first circumference when the endoprosthesis is in the enlarged, deployed configuration, and the second plurality of web elements are arranged at a second angle from 75 degrees to 90 degrees with respect to the longitudinal axis along the second circumference longitudinally spaced from the first circumference when the endoprosthesis is in the enlarged, deployed configuration.

* * * * *